(12) United States Patent
Davison (10) Patent No.: US 7,823,468 B2
(45) Date of Patent: Nov. 2, 2010

(54) VALVE (75) Inventor: Dale A. Davison, Greenwood, NE (US)

(73) Assignee: Teledyne Isco, Inc., Lincoln, NE (US)

( * ) Notice: Subject to any disclaimer, the term of this patent is extended or adjusted under 35 U.S.C. 154(b) by 656 days.

(21) Appl. No.: 11/698,368

(22) Filed: Jan. 26, 2007

(65) Prior Publication Data

US 2008/0178693 A1    Jul. 31, 2008

(51) Int. Cl.
*G01N 30/20* (2006.01)
*F16K 11/085* (2006.01)

(52) U.S. Cl. ............... 73/863.73; 73/61.56; 73/61.55; 137/625.16

(58) Field of Classification Search ............. 73/863.73, 73/61.55–61.56, 864.11; 137/625.16, 625.46
See application file for complete search history.

(56) References Cited

U.S. PATENT DOCUMENTS

| | | | |
|---|---|---|---|
| 3,940,994 A | 3/1976 | Klee et al. | |
| 3,960,003 A | 6/1976 | Beyer et al. | |
| 3,961,534 A | 6/1976 | Gundelfinger | |
| 3,975,946 A | 8/1976 | Ball et al. | |
| 3,999,439 A | 12/1976 | Munk | |
| 4,242,909 A | 1/1981 | Gundelfinger | |
| 4,444,066 A | 4/1984 | Ogle et al. | |
| 4,476,731 A | 10/1984 | Charney et al. | |
| 4,526,686 A | 7/1985 | Sisti et al. | |
| 4,939,943 A | 7/1990 | Strohmeier | |
| 5,616,300 A * | 4/1997 | Ford et al. ............ | 422/103 |
| 6,309,541 B1 | 10/2001 | Maiefski et al. | |
| 6,382,035 B1 | 5/2002 | Nichols | |
| 6,453,929 B1 * | 9/2002 | Johnson et al. ........ | 137/15.05 |
| 6,508,938 B2 | 1/2003 | Maiefski et al. | |
| 6,526,812 B2 | 3/2003 | Martin et al. | |
| 6,576,125 B2 | 6/2003 | Berger et al. | |
| 6,802,969 B2 | 10/2004 | Tanimura | |
| 2001/0013494 A1 | 8/2001 | Maiefski et al. | |
| 2003/0034307 A1 | 2/2003 | Berger et al. | |
| 2003/0094415 A1 | 5/2003 | Tanimura | |
| 2005/0194318 A1 | 9/2005 | Ozbal et al. | |
| 2005/0236314 A1 | 10/2005 | Neyer et al. | |

* cited by examiner

*Primary Examiner*—Thomas P Noland
(74) *Attorney, Agent, or Firm*—Vincent L. Carney (57) ABSTRACT

A sample injector includes a rotary valve element with a straight passageway through it, which element may be rotated to connect a port communicating with a source of solvent with a port communicating with an inlet to a column. Another passageway connects two adjacent ports. The valve element may be rotated to one position in which it provides a straight path for sample to be injected, a second position in which it provides a path that connects a source of purge gas to the chromatographic system and a third position in which it provides a path that connects solvent to the column for preconditioning.

4 Claims, 6 Drawing Sheets

VALVE

BACKGROUND OF THE INVENTION

This invention relates to valves for sample injection in liquid chromatography.

Sample injector valves are known which have a stator, a rotor and ports with the rotor being movable in position to connect pairs of ports. The prior art sample injector valves have bends or corners in passageways between the sample inlet port or a point upstream from the sample inlet port that is connected to the source of sample and the injection port that is connected to the column inlet. One such prior art sample injection system is disclosed in U.S. Pat. No. 3,999,439 issued Dec. 28, 1976. These prior art sample injection valves have a disadvantage in that, when used for some preparatory chromatographic separations such as for example flash chromatography separations, the conduits carrying the sample may become clogged because of the large amount of sample being used.

SUMMARY OF THE INVENTION

Accordingly, it is an object of the invention to provide a sample injection valve that resists clogging.

It is a further object of the invention to provide a sample injection valve with a straight smooth passageway in one of its positions between a source of sample and an inlet of a chromatographic column.

It is a still further object of the invention to provide a sample injection valve in which there are no bends or obstructions between an inlet of a valve where it receives sample and an outlet of the valve.

It is a still further object of the invention to provide a sample injection valve with a straight smooth passageway between two ports spaced 180 degrees apart during sample injection and which can be switched from position to position for other operations such as purging and column preconditioning.

It is a still further object of the invention to provide a single valve element with a smooth passageway between a first and second opening spaced 180 degrees from each other and a second passageway between a third and a fourth opening, which openings can be switched from port to port to communicate with components of the liquid chromatograph.

In accordance with the above and further objects of the invention, a sample injection valve has a central valve element with two passageways within it. A first passageway is between a first and second opening 180 degrees spaced from each other. There are no bends or obstructions in this first passageway. A second passageway is between two other adjacent openings. All four openings rotate together with the valve element.

In use, an actuator moves the valve element from position to position. In one rotary position, the first opening communicates with a source of sample and the second opening communicates with an inlet to a chromatographic column. A solvent system pumps solvent through the injection valve to move the sample into the column and to separate its components. In another rotary position, a third opening communicates with a source of solvent and a fourth opening communicates with the column. In this position, the column can be preconditioned by the solvent system before applying a sample. In still another position, the an opening communicates with a source of purge gas and an opening connected to it by the second passageway communicates with tubing for purging.

With this valve, a preparatory-sized sample may be injected into a column through the valve and follow a straight smooth passageway without obstructions to the column with the sample. Prior to injecting the sample, the valve may connect the column to the solvent supply to supply solvent to the column for preconditioning, and after a chromatographic run, the valve may connect the chromatographic system to a source of purge gas.

As can be understood from the above description, the injection valve from this invention has several advantages such as: (1) it is simple in construction and easily formed of inexpensive material; (2) it is simple in operation moving a single valve element to connect combinations that permit purging, and preconditioning with ease and also permitting injection of sample in a straight through flow passageway with no bends or obstructions so as to reduce plugging of sample during preparatory liquid chromatography.

BRIEF DESCRIPTION OF THE DRAWINGS

The above noted and other objects of the invention will be more fully understood when considered in connection with the accompanying drawings in which.

DETAILED DESCRIPTION

Figure 1:
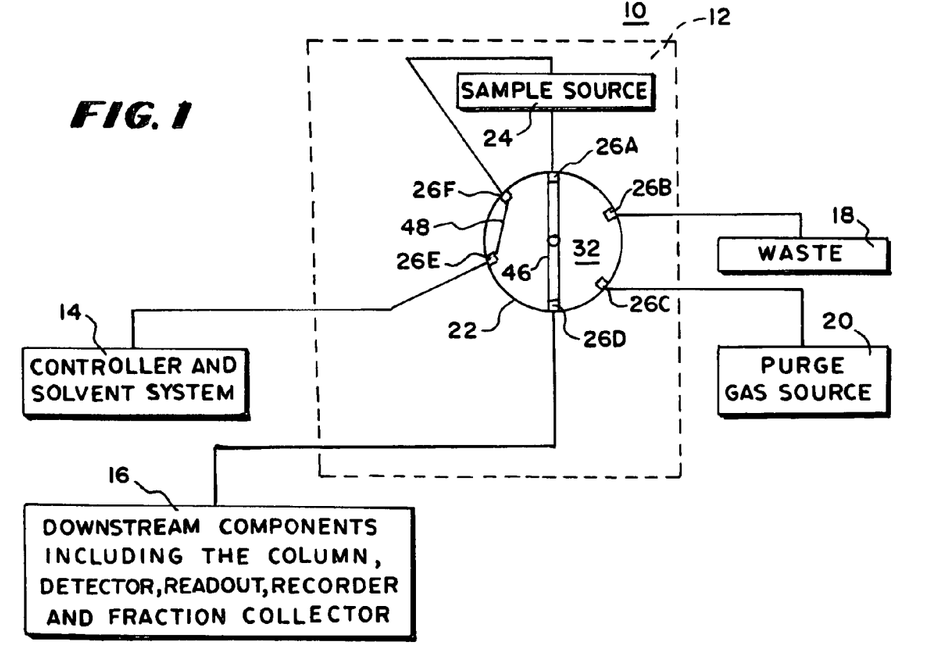
FIG. 1 is a partly schematic and party block diagram of a liquid chromatographic system.

In FIG. 1, there is shown a partly schematic, partly block diagram of a liquid chromatographic system 10 used for preparatory separations including a sample injection valve 12, a controller and solvent system 14, downstream components 16, a waste location 18 and a purge gas source 20. The downstream components 16 are a column, detector, readout, recorder and fraction collector. With this arrangement, the sample injection valve 12 in the preferred embodiment is sized for preparatory applications and includes a source 24 for the samples and a six port valve 22. The valve 22 includes a valve element 32 within its housing having a through smooth passageway 46 and an adjacent-opening connecting slot 48. In the preferred embodiment, the actuator 32 may be manually moved from position to position and includes six ports 26A-26F.

In the preferred embodiment, the smooth passageway 46 connects ports that are 180 degrees spaced from each other to provide a smooth passageway from the outlet of a sample cartridge, a multiple sample cartridge or other source of sample. such as for example sample that is injected by pressure from a larger body of sample into the column or into an input loop for the column and then moved by solvent from the controller and solvent system 14 into the column. In this specification, the words, "smooth passageway" mean a passageway that has no sharp bends that might cause the sample to clog the injector if the injector were to receive a preparatory-sized sample. There should be neither corners nor arcs that have an angle of less than 20 degrees. A smooth passageway through a valve element is between a port on one side of the valve element to a port on the opposite side of the valve element within a range of 170 degrees and 190 degrees from the opposite port and preferably 180 degrees from the opposite port. In this specification the words, "preparatory-sized sample" means a sample size used for preparatory liquid chromatography. The amount of sample injected for a run will vary with the material to be separated. In this specification, the amount of sample is related to the size of the sample needed and the size of the sample injection valve available and useful for the separation.

Figure 2:
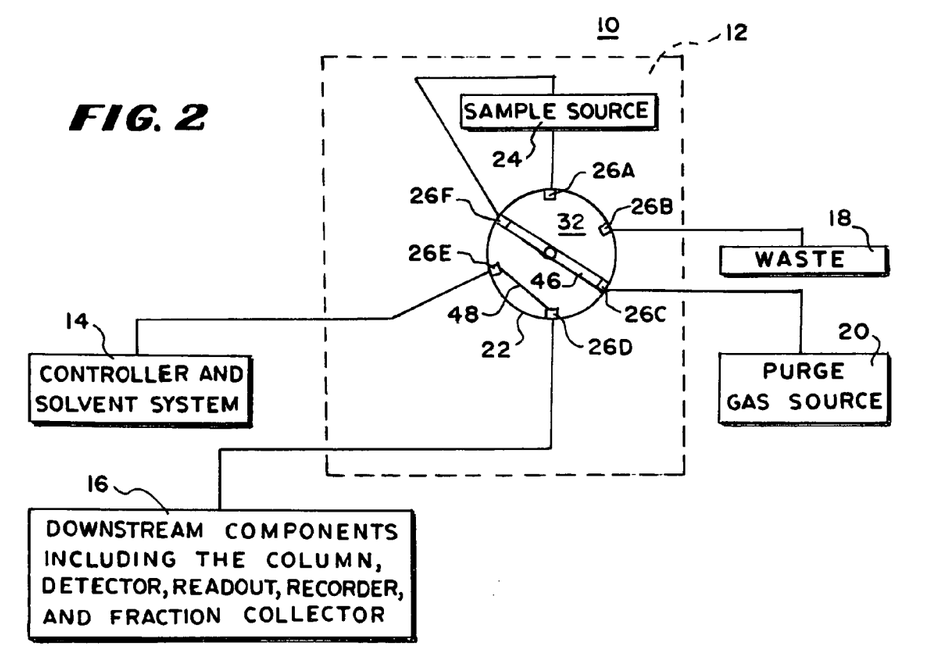
FIG. 2 is a schematic drawing of a valve used in the chromatographic system of FIG. 1 in one position of operation.

In FIG. 2, there is shown a schematic diagram of the chromatographic system 10 with the valve positioned for preconditioning of the column of the liquid chromatographic system 10. In this position, the inlet port 26E receives solvent from the controller and solvent system 14. The solvent flows through the adjacent-opening connecting slot 48 to the port 26D to precondition the column. At this time, the smooth passageway 46 communicates between ports 26F and 26C and no solvent flows through it or through the sample cartridge connecting ports 26F and 26A.

Figure 3:
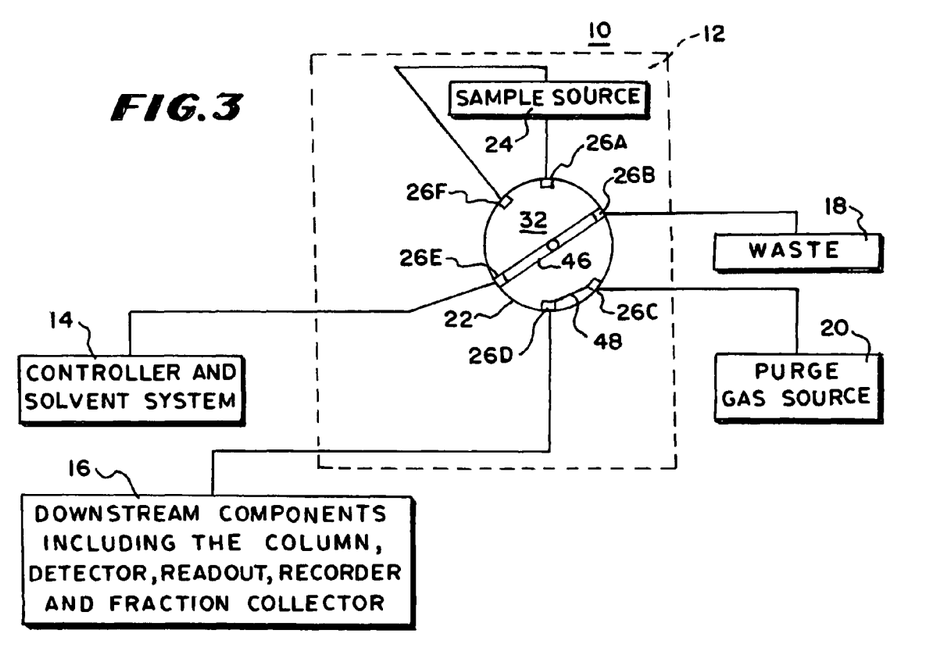
FIG. 3 is a schematic diagram of a sample injection valve useful in the embodiment of FIG. 1 in still another position of operation.

In FIG. 3, there is shown a schematic diagram of the chromatographic system 10 with the valve 22 in position for a purging operation. During the operation, the smooth passageway 46 communicates with ports 26E and 26B to wash tubing between the solvent supply and waste with solvent, and the purged gas source 20 communicates through the adjacent-opening connecting slot 48 between port 26C and port 26D to supply purging air to the column within the downstream components 16 including the column, detector, readout, recorder and fraction collector.

The six ports, 26A-26F, of the valve 22 are connected so that three positions of the rotor provide the connections for: (1) sample injection and a chromatograph run; (2) a purge operation; and (3) preconditioning of the column. For this purpose, the port 26A is connected to the outlet of the sample source 24, the port 26B is connected to waste 18, the port 26C is connected to the purge gas source 20, the port 26D is connected to the downstream components 16 to purge the column and fraction collector, the port 26E is connected to the controller and solvent system 14 and the port 26F is connected to the inlet of the sample source 24. The valve element 32 includes the smooth passageway 46 and an adjacent-opening connecting slot 48 connecting the two openings between the end of the smooth passageway 46.

In operation, a preparatory-sized sample or preparatory-sized samples is inserted into the sample source 24 and after fluid has flown between the controller and solvent system 14 to condition the column, a sample is injected into the column of the downstream components 16 for separation and collection in the fraction collector. When the valve element is in the first of the three positions (FIG. 1), the solvent source is connected to the column through port 26E, adjacent-opening passageway 48, port 26F, the inlet to the sample source 24, port 26A, smooth passageway 46 and port 26D. When the valve is moved to second position, the smooth passageway 46 moves from a position between port 26A and 26D to a position between port 26F and port 26C, the adjacent opening connection passageway 48 moves from a location connecting port 26F and port 26E to a location connecting port 26E and port 26D. In the second position (FIG. 2), the solvent source is connected to the column for preconditioning through port 26E, adjacent-opening passageway 48, and port 26D. In this position the purge gas source 20 is connected to port 26A, which is blocked by the valve element through port 26C, smooth passageway 46, port 26F and the sample source 24. In the third position (FIG. 3), the solvent source is connected to waste through port 26E, smooth passageway 46 and port 26B. The purge gas source is connected to the column, controller and solvent system 14 through port 26C, adjacent-opening passageway and port 26D.

Figure 4:
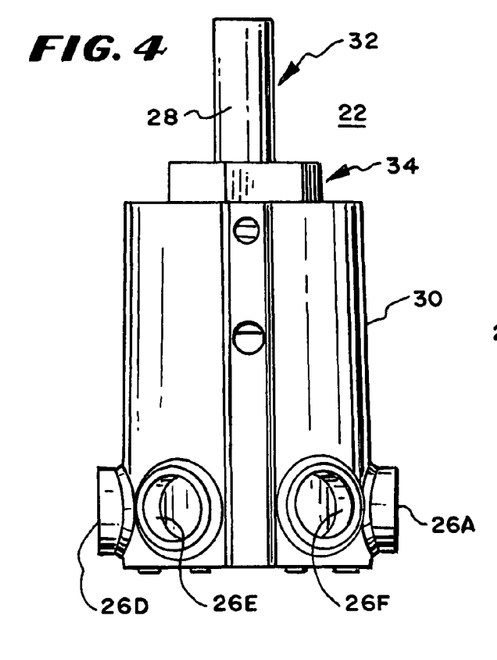
FIG. 4 is an elevational view of a sample injection valve in accordance with an embodiment of the invention.

In FIG. 4, there is shown the front elevational view of the valve 22 having a shaft 28 for the rotor 40 (now shown in FIG. 4; shown in FIGS. 6-9), a valve body or housing 30, an adjustment nut 34, and six circumferentially spaced outlet ports 26A-26F (only ports 26A, 26D, 26E, and 26F being shown in FIG. 4). With this arrangement, the shaft 28 for the rotor 40 may be manually or automatically rotated from position to turn the actuator 32 (only the shaft 28 of the rotor 40 being shown in FIG. 4) to either inject a sample and perform separation, perform a purging operation or a preconditioning operation. The appropriate connections are made when going from position to position in the single operation of turning the shaft 28 for the rotor 40.

Figure 5:
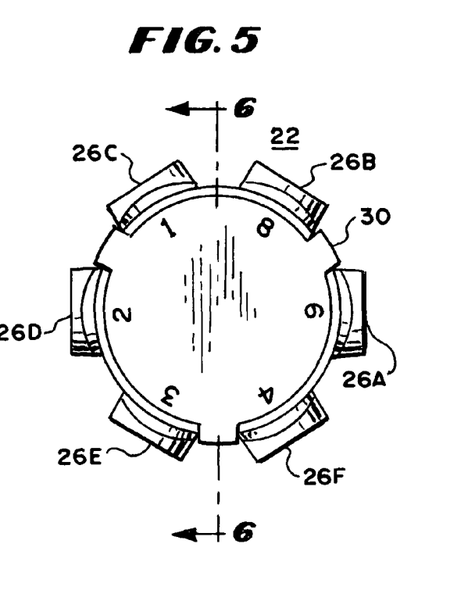
FIG. 5 is a bottom view of the valve of FIG. 4.

In FIG. 5, there is shown a bottom view of the sample injection valve 22 showing the outlet ports 26A-26F shaped to receive the proper connections, which are generally tubing (for operation of the chromatographic system 10).

Figure 6:
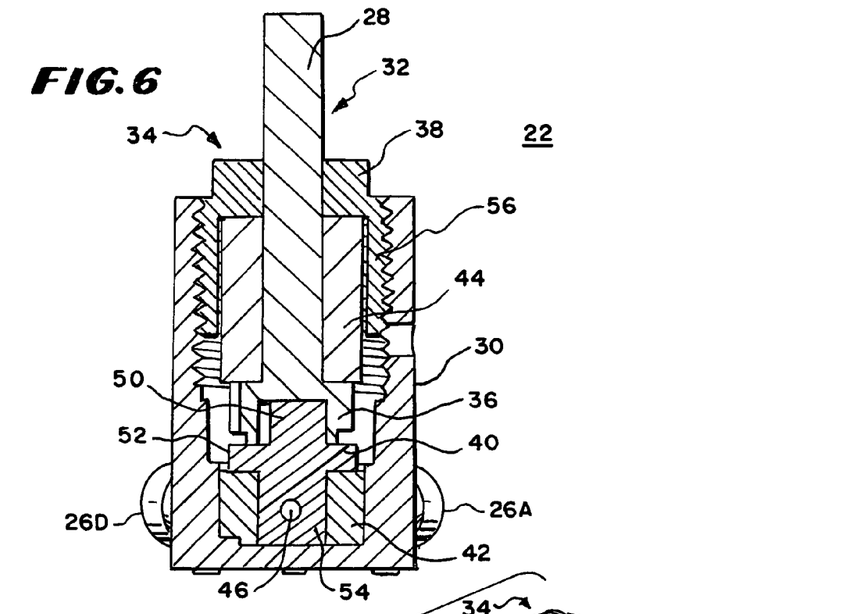
FIG. 6 is a sectional view taken through lines 6-6 of FIG. 5.

In FIG. 6, there is shown an elevational sectional view taken through lines 6-6 of FIG. 5 showing the valve body 30, the actuator 32, the adjustment nut 34, the rotor 40, a stator 42 and a spacer 44. These parts cooperate together so that when the actuator 32 is rotated, the rotor 40 turns to connect two ports that are spaced from each other by 180 degrees and at the same time to connect two other ports that are adjacent to each other.

For this purpose, the actuator 32 includes the actuator shaft 28 that extends on one end through the adjustment nut 34 outside of the valve body 30 and at the other end includes a socket 36 that receives a plug 50 of the rotor 40. The cylindrical tubular spacer 44 and the tubular adjustment nut 34 rotatably support the actuator shaft 28 along the center of the housing 30 so as to rotate the socket 36. The socket 36 includes a flattened portion that engages a flattened portion of the plug 50 so as to rotate the rotor 40 along with the rotation of the actuator shaft 28. To tighten the actuator 32 to the proper tension for rotation, the adjustment nut 34 includes a hexagonal head 38 and an externally threaded bore 56 sized to engage the outer periphery of the cylindrical tubular spacer 44 and to engage threads in the upper end of the valve body 30 so that it may be tightened downwardly forcing the spacer 44 down against the shoulder of the actuator socket 36.

The rotor 40 has an annular center rotary guide or flange 52 with the plug 50 at its upper end shaped to be received within the actuator socket 36 and at its lower end beneath the annular center rotary guide or flange 52 is cylindrical rotor body 54 serving as a valve element. The rotor body 54 includes the smooth passageway 46 and the adjacent open passageway 48 (the adjacent open passageway 48 is not shown in FIG. 6). To support the annular center flange 52, the cylindrical stator 42 rests at the bottom of the valve body 30 and is held stationary thereto so that the rotor 40 rotates within its cylindrical opening.

Figures 7, 8:
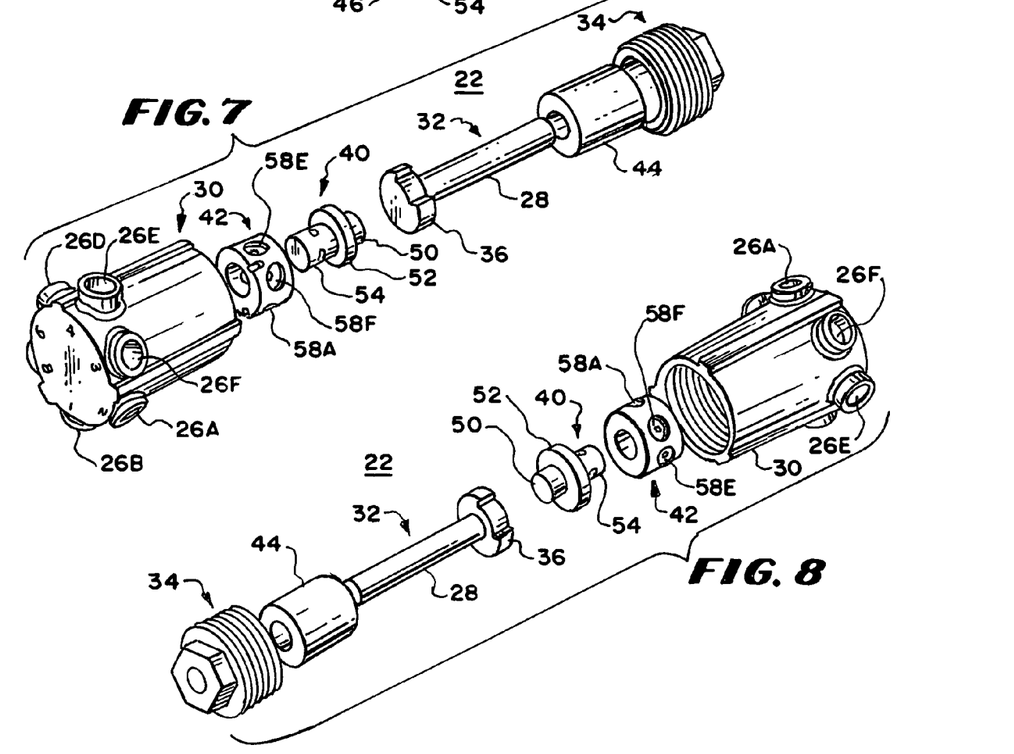
FIG. 7 is a an exploded perspective view of the valve of FIG. 4 from one viewpoint.
FIG. 8 is a perspective exploded view of the valve of FIG. 1 from another viewpoint.

In FIG. 7, there is shown an exploded perspective view of the valve 22 showing the valve body 30, the stator 42, the rotor 40, the actuator 32, the spacer 44 and the adjustment nut 34 in that order. In this view, it can be shown how the rotor 40 is positioned to align its smooth passageway with ports 180 degrees apart to provide a straight line flow path and at the same time connect to adjacent ports. With this arrangement, a sturdy simple valve 22 is provided which is singularly free of plugging under heavy sample loading such as in preparatory liquid chromatography. It is singularly free of blocking and plugging because there is a straight smooth passageway with no bends from the source of the sample 24 (FIGS. 1-3) to the output of the valve where it will enter the chromatographic column.

In FIG. 8, there is shown another exploded perspective view taken from the reverse angle so as to more clearly show the manner in which the plug 50 of the rotor 40 fits into the socket 36 of the actuator 32 and the rotor 40 cooperates with the stator 42 to align openings through the stator 42 to the outlet ports of the valve body 30. As shown in FIGS. 7 and 8, the stator 42 includes a plurality of such openings 58A-58F (58E and 58F shown in FIGS. 7 and 58A, 58E and 58F shown in FIG. 8) that align with the ports 26A-26F (26A, 26B, 26E and 26F shown in FIGS. 7 and 26A, 26E and 26F shown in FIG. 8).

Figure 9:
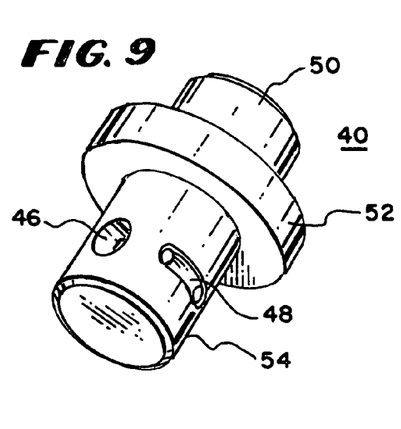
FIG. 9 is a perspective view of a rotor used in the valve of FIG. 7.

In FIG. 9, there is shown a perspective view of the rotor 40 having the rotor body 54, the annular central flange 52 and the plug 50. As shown in this view, the rotor body 54 includes the smooth passageway 46 and the adjacent open passageway 48 which is a slot able to form a channel between two adjacent openings and being positioned between the opposite ends of the smooth passageway 46 so as to be 90 degrees at its center point between the ends of the smooth passageway 46. In this manner, it connects the two adjacent ports that are between the two end ports of the smooth passageway 46 so that as the rotor 40 moves, adjacent openings are connected to provide a passageway for solvent in and out of the valve 12 (FIG. 6) and for solvent carrying the sample and sample components straight through the valve element 54 without bends to the column.

Figure 10:
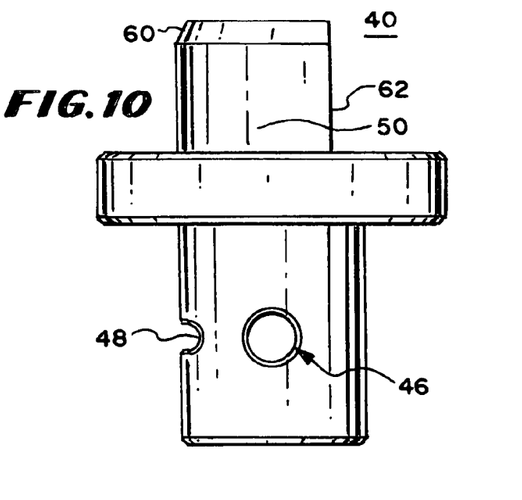
FIG. 10 is an elevational view from one angle of the valve of FIG. 9.

In FIG. 10, there is shown a simplified, elevational front view of the rotor 40 better illustrating the smooth passageway 46 and the adjacent opening connecting slot 48 on opposite sides of the central flange 52. At the upper end, the plug 50 is shown having beveled upward end 60 and a flat cut side 62. The beveled end 60 provides easing and centering and the flat cut side 62 securely grips the flat portion of the actuator socket 36 so as to cause the rotor 40 to turn as the actuator 32 is turned.

Figure 11:
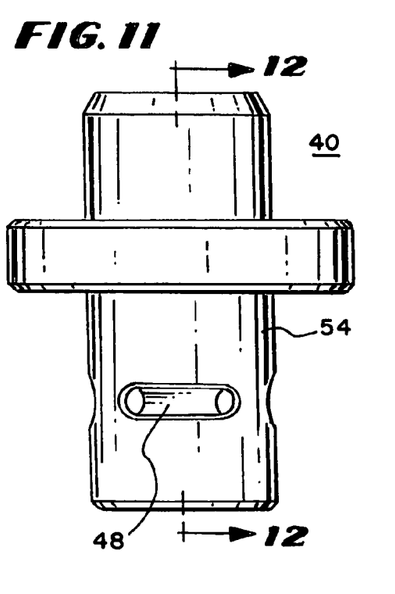
FIG. 11 is side elevational view of the valve of FIG. 9 from another angle.
Figure 12:
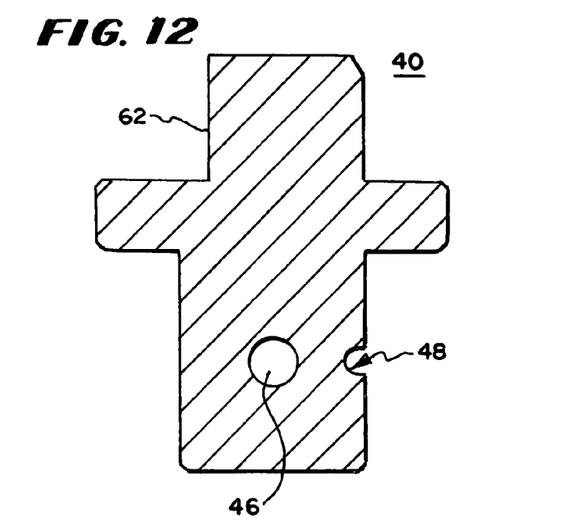
FIG. 12 is a sectional view taken through lines 12-12 of FIG. 11.
Figure 13:
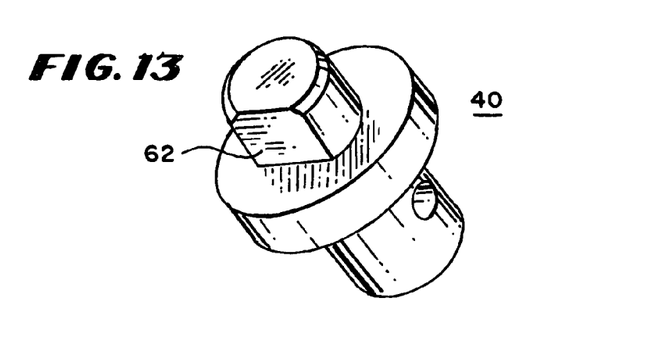
FIG. 13 is a perspective view of the valve element of FIG. 9 taken from another viewpoint.

To more completely illustrate the structure of the rotor 40, FIG. 11 is a side simplified elevational view of the rotor 40 showing the adjacent opening passageway 48 most clearly at the bottom of the rotor body 54, FIG. 12 is an elevational view taken through lines 12-12 of FIG. 11, showing the through smooth passageway 46 more clearly and the cut-away flat side 62 and FIG. 13 is a perspective view of the rotor 40 from another angle more clearly showing the flat cut-away portion 62 that grips the corresponding flat portion on the inside of the actuator socket 36.

Figure 14:
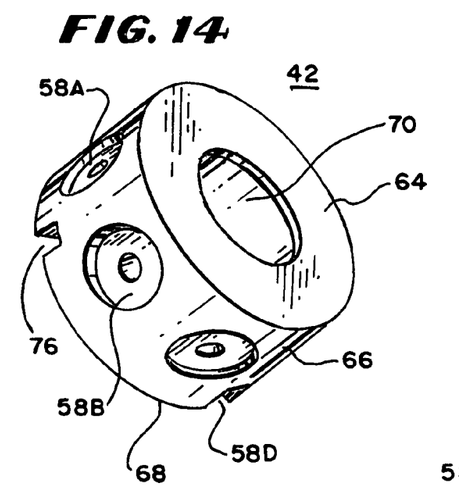
FIG. 14 is a perspective view of the stator used in the valve of FIG. 7.

In FIG. 14, there is shown a perspective view of the stator 42 having an annular top wall 64, a cylindrical outer wall 66 and an annular bottom wall 68 to form a tubular cylinder with a cylindrical opening 70 adapted to receive the rotor body 56 rotatably within its center. Spaced around its outer periphery are cylindrical bores with openings extending through to the inner cylindrical opening 70 shown at 58A-58C in FIG. 14 (opening 58D-58F not being shown in FIG. 14). These central openings align with the ports 26A-26F and are firmly held in position therewith (FIG. 5). At the bottom end 68 at the edge where the bottom end 68 joins the side wall 66, there are a plurality of spaced apart grooves 76 that engage corresponding upward detents in the bottom of the valve body 30 to hold the stator 42 from rotating with the rotor 40.

Figure 15:
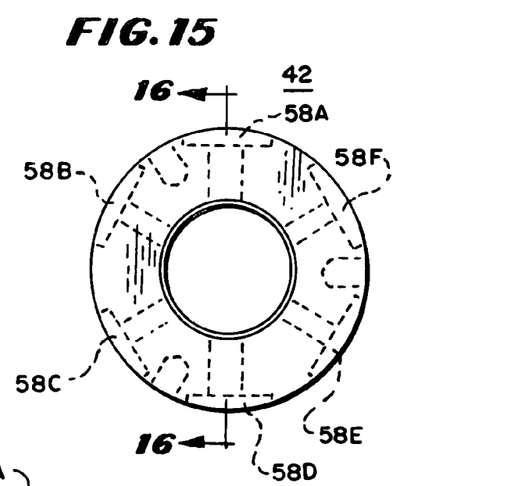
FIG. 15 is a top view of the stator of FIG. 14.
Figure 16:
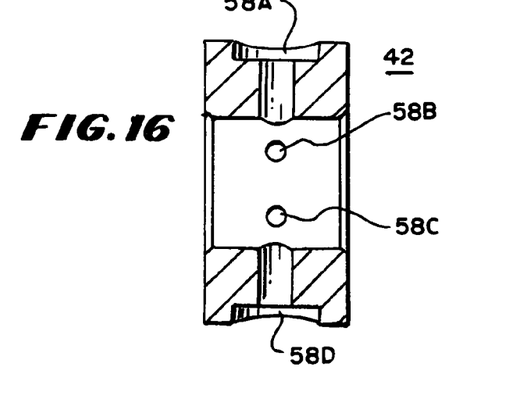
FIG. 16 is a sectional view of the stator of FIG. 14 taken through lines 16-16 of FIG. 15.
Figure 17:
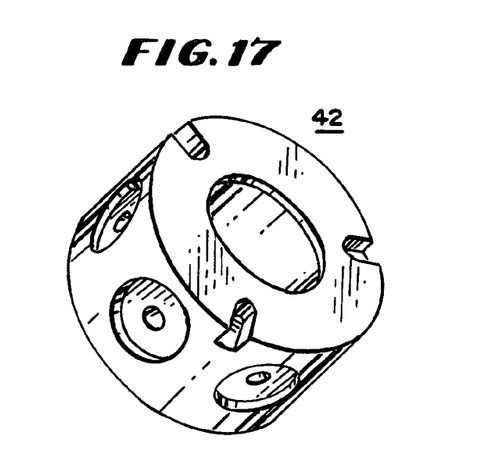
FIG. 17 is a perspective view of the stator of the FIG. 14 taken from another viewpoint.
Figure 18:
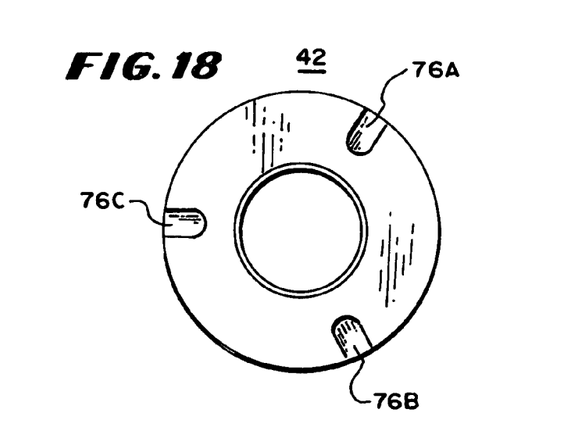
FIG. 18 is a bottom view of the stator of FIG. 17.

In FIG. 15, there is shown a top view of the stator 42 showing the cylindrical bores with central openings 58A-58F with the central openings extending through to the cylindrical opening 70 of the stator 42. In FIG. 16, there is shown a sectional view of the stator 42 taken through lines 16-16 of FIG. 15 showing more clearly that the opening 58A and 58D extend into the cylindrical opening 70 from the outer curved periphery. In FIG. 17, there is shown a perspective view of the stator 42 looking from the opposite end to show the cylindrical bores with central openings and grooves 76 which fit into the detents in the bottom of the valve body 30 to maintain the stator stationary. In FIG. 18, there is shown a bottom view of the rotor 40 showing the location of the three grooves 76A-76C.

Figure 19:
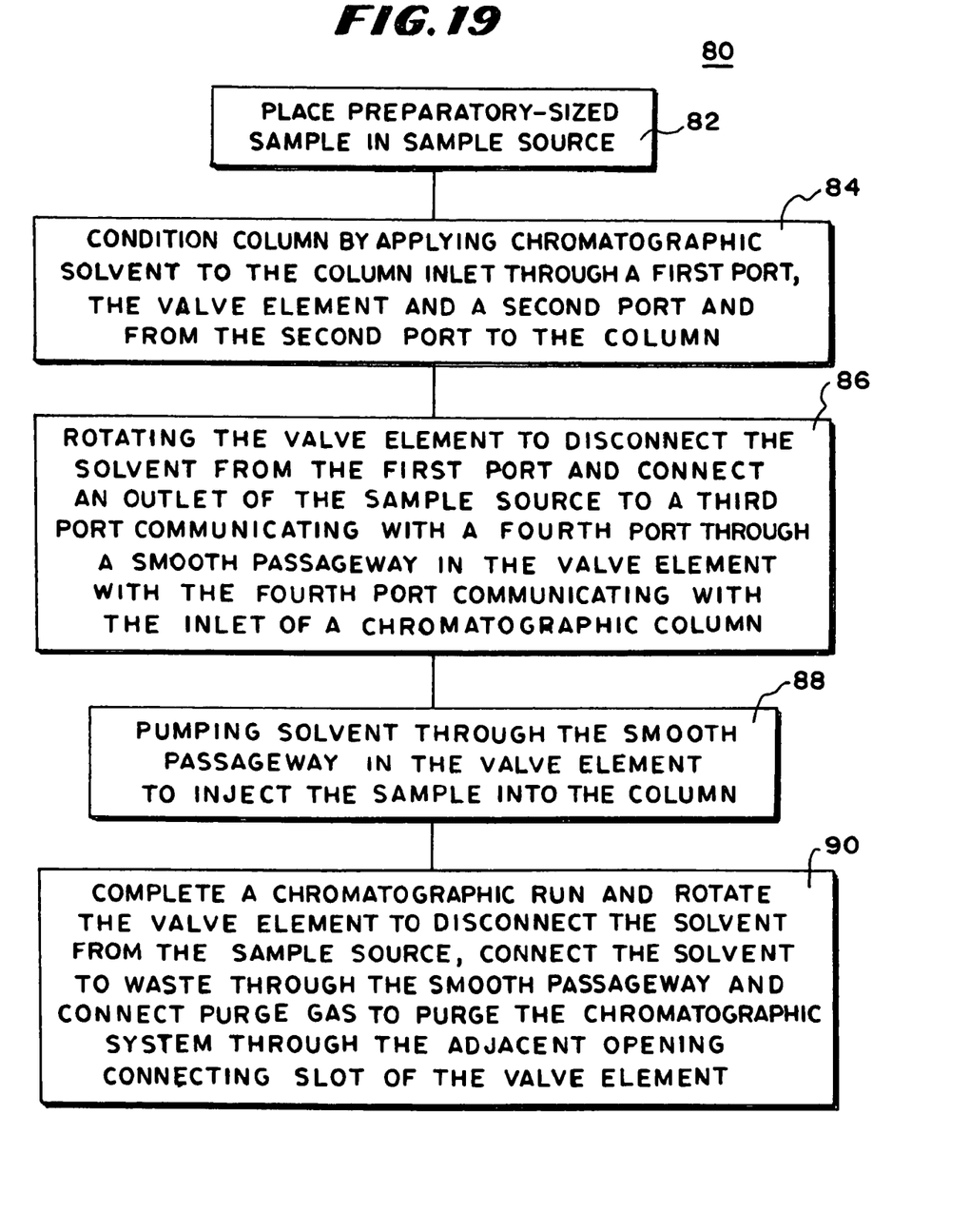
FIG. 19 is a flow diagram of a process for preparatory liquid chromatography.

In FIG. 19, there is shown a flow diagram of a process 80 for performing preparatory liquid chromatography using the sample injection valve 12 in accordance with an embodiment of the invention having the step 82 of placing a preparatory-sized sample in the sample source. The sample source may be a single sample cartridge or a multiple cartridge or the samples may be drawn from a body of sample and pumped into a sample injector. All of these techniques are known in the art and are not in themselves part of the invention.

When the sample is in the cartridge, the chromatographic column is conditioned as shown in step 84 by applying chromatographic solvent to the column through the first port and the valve element to a second port of the valve and from the second port to the column. When the chromatographic column has been preconditioned such as by becoming pressure stable, the valve element is rotated to disconnect the solvent from the valve element and connect an outlet of the sample source to an inlet of the chromatographic column through a third port, a smooth passageway through the valve element and from a second port to the inlet of the column as shown at step 86. Solvent is then pumped through the cartridge to carry the sample through the smooth passageway in the valve element and inject the sample into the column as shown at step 88. Once the sample is in the column, the chromatographic run is completed and the element is rotated to disconnect the solvent from the sample source, connect to waste 18 through the smooth passageway 46 to wash the tubing, and connect purged gas source 20 through the chromatographic system through the valve element as shown at step 90.

As can be understood from the above description, the injection valve from this invention has several advantages such as: (1) it is simple in construction and easily formed of inexpensive material; (2) it is simple in operation moving a single valve element to connect combinations that permit purging, and preconditioning with ease and also permitting injection of sample in a straight through flow passageway with no bends or obstructions so as to reduce plugging of sample during preparatory liquid chromatography.

While the preferred embodiment of the invention has been described in considerable detail, it is to be understood that, within the scope of the appended claims, the invention may be practiced other than as specifically described.

What is claimed is:

1. A sample injection valve for preparatory liquid chromatography comprising:
   at least one rotor;
   actuator means for moving the at least one rotor from position to position;
   a plurality of output ports;
   each of said output ports being alignable with a corresponding opening in said at least one rotor;
   said at least one rotor having a straight smooth passageway through its center whereby ports spaced 180 degrees from each other may communicate when the at least one rotor is in a first position;
   said at least one rotor having a connecting channel having a first channel end and a second channel end;
   the first channel end of said connecting channel communicating with a third port and the second channel end communicating with a fourth port;
   said third and fourth ports being between a first port and a second port whereby said at least one rotor rotates from position to position, said ports spaced 180 degrees from each other communicate with each other and adjacent ports communicate with each other; wherein said first port is adapted to communicate through a sample holder with a source of chromatographic solvent and said second port is adapted to communicate with a chromatographic column through a passageway that extends from said sample holder to said chromatographic column;
   said passageway being a smooth passageway.

2. A sample injection valve in accordance with claim 1 wherein said third port is adapted to communicate with a source of purged gas and said fourth port is adapted to communicate with said communication for purging thereof.

3. A sample injection valve in accordance with claim 2 in which said third port in a second rotary position is adapted to communicate with said source of chromatographic solvent and said fourth port in another position is adapted to communicate with said chromatographic column.

4. A sample injection valve in accordance with claim 3 further comprising a tubular stator, said tubular stator having a cylindrical opening adapted to rotatably receive said at least one rotor and having cylindrical bores spaced around the tubular stator periphery; whereby rotation of the at least one rotor aligns at least one cylindrical bore of the cylindrical bores spaced around the tubular stator periphery with an opening and a corresponding smooth channel in said at least one rotor.

* * * * *